United States Patent [19]
Serbinski et al.

[11] Patent Number: 5,341,534
[45] Date of Patent: Aug. 30, 1994

[54] ELECTRIC TOOTHBRUSH

[75] Inventors: Andrew Serbinski, Annadale, N.J.; Steve O. Mork; Roberta L. Callaghan, both of Fort Collins, Colo.

[73] Assignee: Teledyne Industries, Inc., Fort Collins, Colo.

[21] Appl. No.: 80,003

[22] Filed: Jun. 21, 1993

[51] Int. Cl.$^5$ ............................................. A61C 17/34
[52] U.S. Cl. ..................................... 15/22.1; D4/101
[58] Field of Search .................... 15/22.1, 22.2, 22.4, 15/23, 24, 28, 29; D4/100, 101, 102, 109, 112

[56] References Cited

U.S. PATENT DOCUMENTS

| | | | |
|---|---|---|---|
| D. 197,208 | 12/1963 | Cassidy et al. | D4/101 |
| D. 202,873 | 11/1965 | Husted | D4/101 |
| D. 204,127 | 3/1966 | Syvertson | 15/22.1 X |
| 3,160,902 | 12/1964 | Aymar | 15/22.1 |
| 3,168,834 | 2/1965 | Smithson | 15/22.1 |
| 3,278,963 | 10/1966 | Bond | 15/22.1 |

Primary Examiner—Edward L. Roberts
Attorney, Agent, or Firm—Hugh H. Drake

[57] ABSTRACT

A battery-powered toothbrush has an elongated housing shaped to be grasped by the human hand. The housing encloses a battery-energized motor which drives a brush shaft that has a stub projecting through a nose of the housing and upon which in use a brush is mounted. A generally tubular housing shell confines the battery, motor and shaft. An upper half shell is of a U-shaped exterior cross section over a substantial portion of its length, while a lower half shell is mated to the upper half shell in definition of the housing and is of semi-cylindrical exterior cross-section over a like substantial portion of its length. The distance along those substantial portions approximates the width of the adult human hand. The shaft is offset downwardly from the longitudinal geometric axis. All shell portions of different diameter merge smoothly into other portions of the shell.

6 Claims, 5 Drawing Sheets

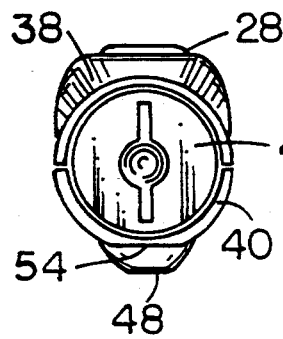
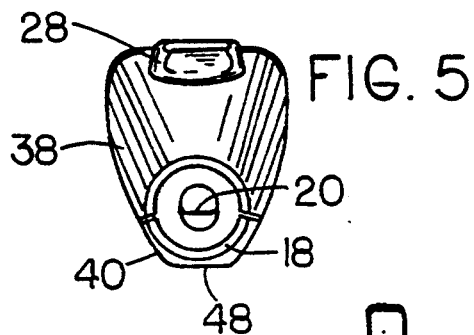
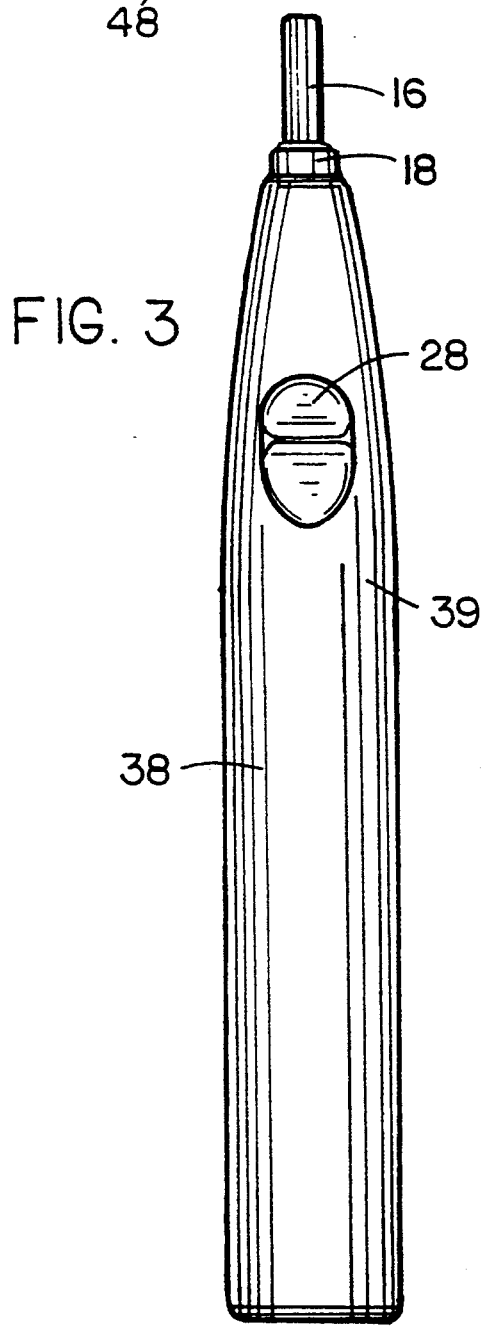
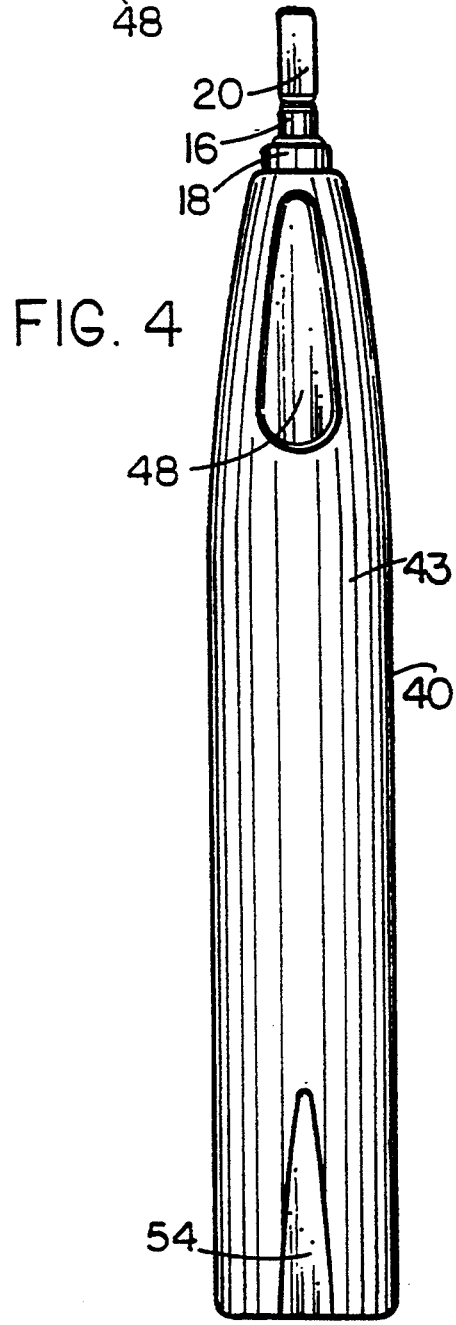

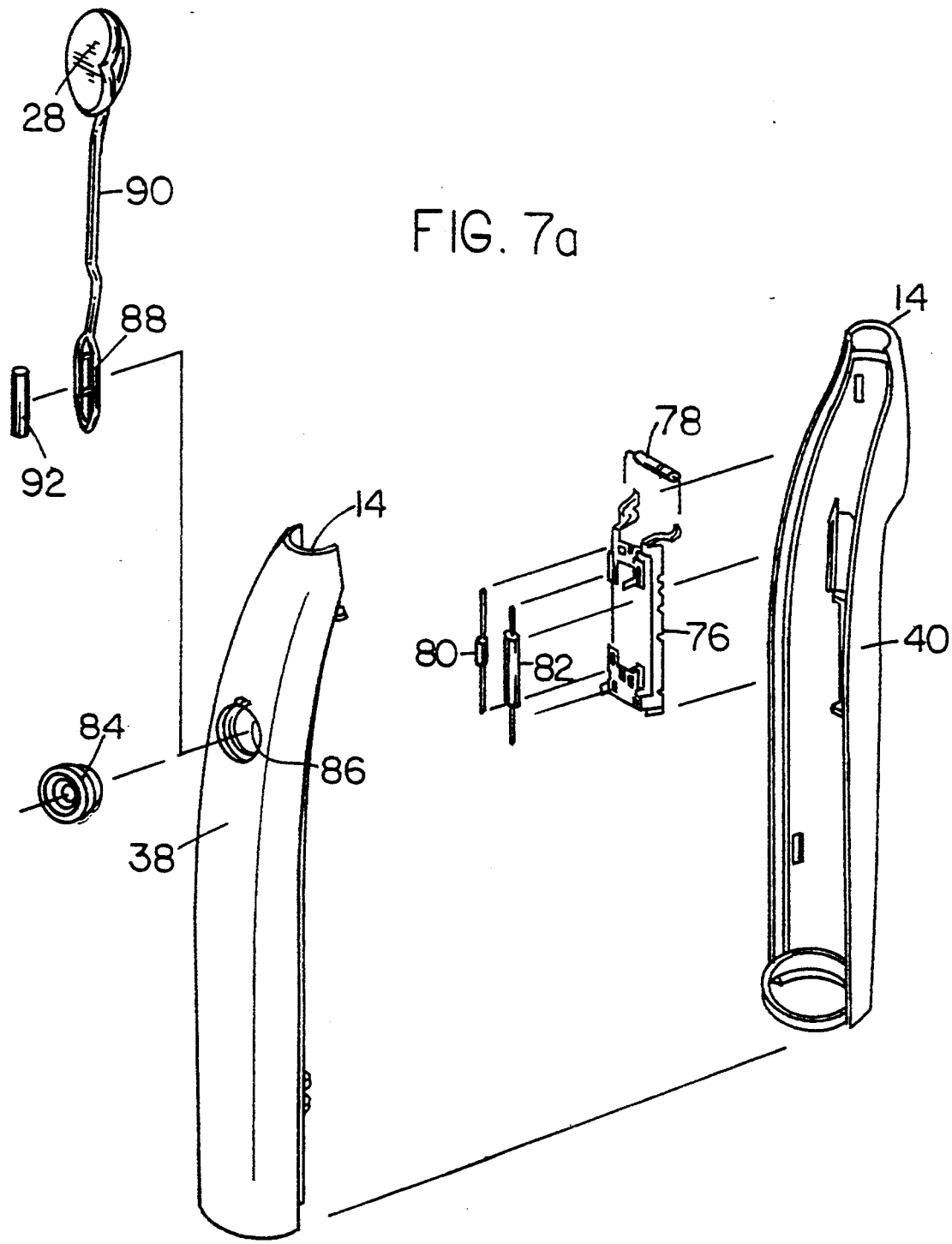

ELECTRIC TOOTHBRUSH

The present invention pertains to electric toothbrushes. More particularly it relates to an electric toothbrush with an outer shell having a configuration particularly accommodative of the hand.

Battery-powered electric toothbrushes typically have an elongated tubular housing from one end of which a shaft emerges. In accommodation of the internal components, the housing usually is of round cross section. Exemplary background references are U.S. Pat. No. 3,277,358-Nicholl, U.S. Pat. No. 3,418,552-Holmes, U.S. Pat. No. 3,463,994-Spohr, U.S. Pat. No. 3,510,747-Petrides, U.S. Pat. No. 3,480,795-Roszyk et al, and U.S. Pat. No. 4,374,354-Petrovic et al.

It is an object of the present invention to provide an electric toothbrush with a new and improved housing configuration that conforms naturally to the human hand when grasped thereby.

Another object of the present invention is to provide a new and improved electric toothbrush in which the circumferential configuration of the housing differs significantly as between the upper and lower halves.

A further object of the present invention is to provide a new and improved electric toothbrush in which the nose portion of the housing is displaced to one side of the generally central geometric axis of the remainder of the housing.

In accordance with the present invention, a battery powered toothbrush has an elongated housing shaped to be grasped by the human hand and within which housing are the battery, a motor energized by the battery and a brush shaft driven by the motor with a stub projecting through the nose of the housing for mounting a brush. The housing is of generally tubular shape and is in the form of a shell. An upper half of the shell is of U-shaped exterior cross section over a substantial central portion of its length. A lower half shell is mated to the upper half shell in definition of the housing and is of semi-cylindrical exterior cross section over a like portion of its length. In one particular further aspect, the housing generally has a central longitudinal housing geometrical axis, while the shaft stub projects from a nose portion displaced to one side of that axis. Beyond the central portions to the nose the half shells are smoothly curved laterally in accommodation of that displacement.

The features of the present invention which are believed to be patentable are set forth with particularity in the appended claims. The organization and manner of operation of the invention, together with further objects and advantages thereof, may best be understood by reference to the following description taken in connection with the accompanying drawings, the several figures of which like reference numerals identify like elements, and in which:

FIG. 3 is a front elevational view thereof;

FIG. 4 is a rear elevational view thereof;

FIG. 5 is a top plan view thereof;

FIG. 6 is a bottom plan view thereof;

Figure 7B:
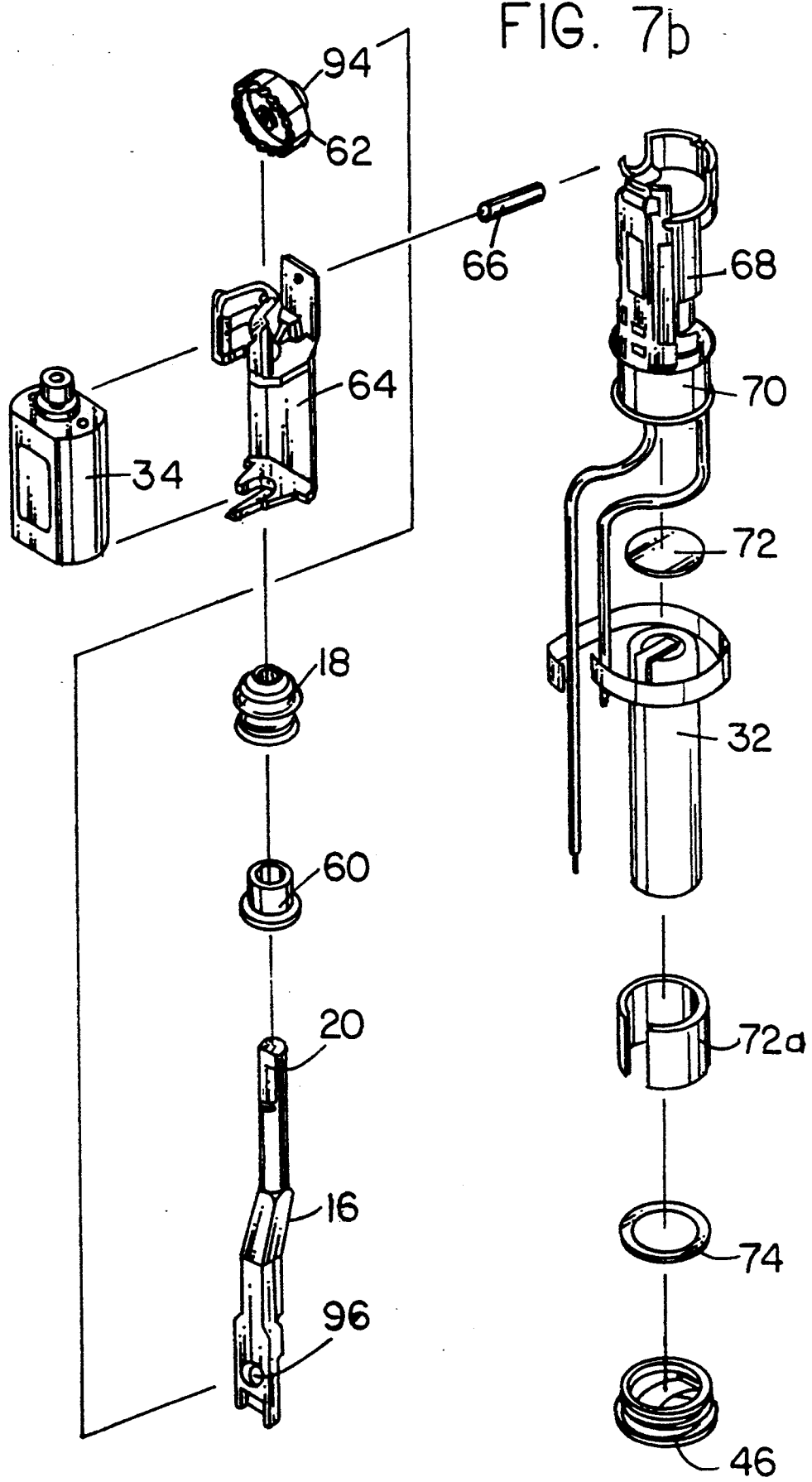

FIGS. 7a and 7b together are an exploded isometric view thereof; and

Figure 8A:
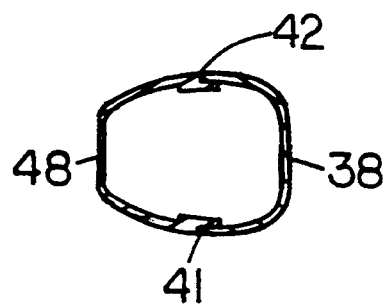
Figure 8B:
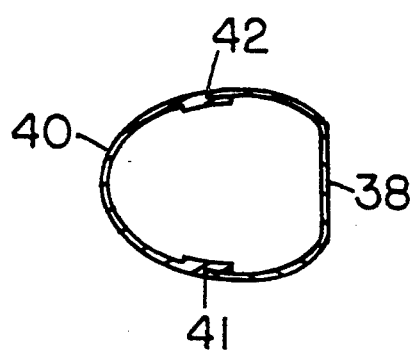
Figure 8C:
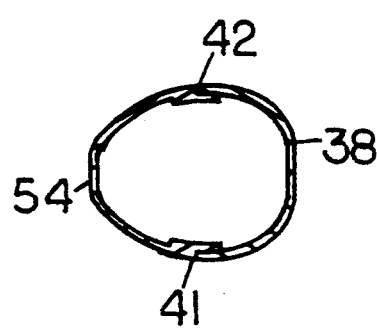
Figure 1:
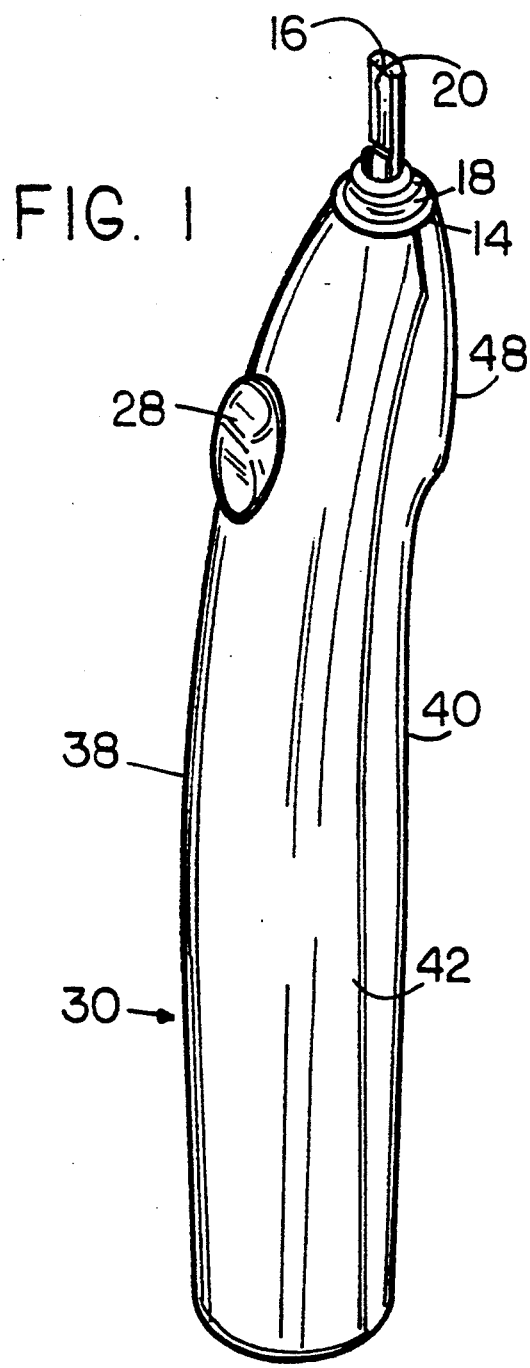
FIG. 1 is an isometric view of an electric toothbrush embodying the present invention.
Figure 2:
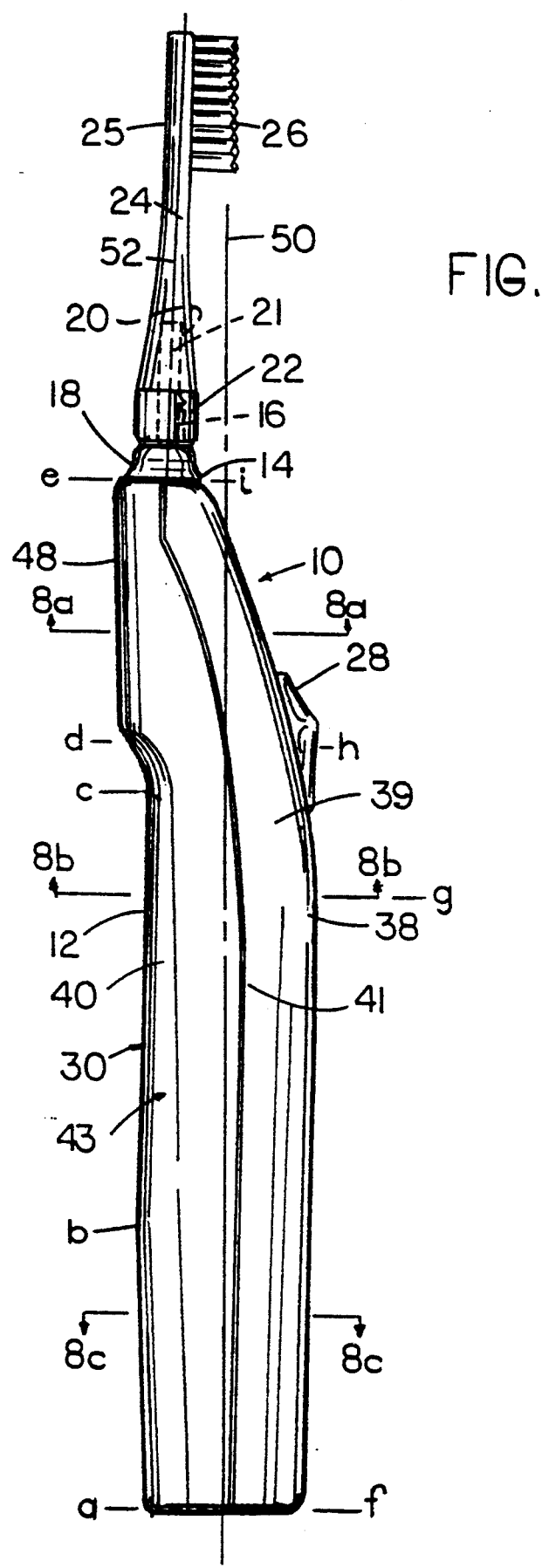
FIG. 2 is a side elevational view thereof.

FIGS. 8a, 8b and 8c are cross sectional views taken along the respective lines 8a—8a, 8b—8b and 8c—8c in FIG. 2 but with all internal components removed.

An electric toothbrush 10 includes an elongated handle 12 from a top end or nose 14 of which projects a shaft 16 through a flexible sealing boot 18. Shaft 16 is cut away to define a flat 20 and form the terminal end portion or stub 21 of shaft 16 into a generally semi-cylindrical shape. The base 22 of the shank 24 of a toothbrush 25 includes a longitudinal well of mating cross-sectional shape so as to be received snuggly on the outer end portion 21 of shaft 16. Over the outer end portion of shank 24 are secured bristles 26 which complete formation of the toothbrush. With handle 12 in its normal somewhat horizontal position for use, bristles 26 point in a direction upwards toward what then is the upper side of handle 12 on which is located an on/off slide button 28.

Directional terms are used herein somewhat arbitrarily. That is, words such as upper, lower, top, bottom and downward are employed consistently only with respect to one another from an assumed frame of reference. In actual use the electric toothbrush may have any spatial orientation.

Handle 12 is the form of an elongated housing 30 shaped to be grasped by the human hand and within which housing are located a battery 32, a motor 34 energized by battery 32 and brush shaft 16 driven by motor 34 and of which stub 21 forms the outer end portion. Thus, shaft 16 projects through boot 18 at what constitutes nose 14.

Housing 30 is a generally tubular shell which in this case is longitudinally split into an upper half shell 38 and a lower half shell 40 with the split occurring at side seams 41 and 42 along the two sides of housing 30. In an alternative embodiment, the two halves of housing 30 may be split midway through what becomes the upper and lower sides of the housing as shown instead of along the sides but this is less preferable because in the form shown the tools for forming the two halves retain symmetry about the longitudinal axis.

Upper half shell 38 has a U-shaped exterior cross section as in FIG. 8b over a substantial and central portion 39 of its length. Referring to FIGS. 2 and 8a-8c, that U-shaped cross section has a bight of substantially constant width. From mark h on toward nose 14 at mark e the width of the bite of the U smoothly narrows. From about opposite mark b to the bottom or end of half shell 38 opposite nose 14 the cross sectional exterior shape of half shell 38 changes gradually and smoothly from a U-shape to a half-cylindrical shape.

Lower half shell 40 mates with upper half shell 38 along side seams 41 and 42. The exterior cross section of half shell 40 over a like substantial central portion 43 of its length is semi-cylindrical. From mark b to mark a at the lower end of half shell 40 that semi-cylindrical shape gradually changes to a cross section of diminishing radius, and forming a flat 54, which at mark a is generally semi-cylindrical so as to define with upper half shell 38 a cylindrical threadway into which is threaded a closing plug 46.

In more exact detail of the instant embodiment it may be observed that seams 41 and 42 over the central region roughly between marks b and d, opposite mark h, are located in the overall circumferential cross section a slight distance toward the U-shape from the semi-cylindrical shape so that lower shell 40 along that margin includes a portion of that which forms the U-shaped cross section. Viewed another way, it could be said that the walls of lower shell 40 in the central region extend a short distance beyond that of a truly semi-cylindrical shape so as to begin the U-shape of the remainder of the circumference.

Beyond about mark c and continuing to the nose at mark e, the width of bottom shell 40 smoothly narrows along seams 41 and 42. At the same time, the central portion of the wall which defines lower shell 40 curves downwardly Al and merges into a generally flat surface 48 running lengthwise of handle 12 and merging smoothly into nose 14 at mark e after having continued from mark d.

Running centrally through handle 12 is a geometric axis 50. Shaft 16 is aligned generally along an axis 52 spaced away from upper shell 38 by an offset distance. When handle 12 in use is grasped by the human hand, the brushhead composed of bristles 26 is spaced by a similar offset distance from the axis defined by the curled fingers which encircle handle 12. It is in accommodation of that offset that the exterior surface of half shell 40 is offset in a smooth transition approximately the same amount from mark c to mark d.

Continuing toward its bottom end from mark b to mark a the exterior surface of lower shell 40 gradually transforms into a true half-cylindrical shape at the lower end and in definition of the threaded margin which receives plug 46. In this transistion between mark b and mark c the outer surface of shell 40 smoothly merges into tapering flat 54.

Of primary interest to the present invention are the different surface shapes which merge smoothly together and establish the feel which is experienced by the user during the brushing of the teeth. That feel is primarily the overall housing shape from about mark d to a little beyond mark b, a distance about the same as the width of the human hand. Also of interest in that connection is the comparative placement of the location of the toothbrush by means of stub 21 so as to be offset laterally from the geometric axis of the handle which is grasped by the user. Because that offset and the grasped surfaces are part of what encloses the operative components internally of housing 12, the nature of the component assembly and the interrelationship of the different component are important in the sense that their arrangement must accommodate the exterior shape of the housing. On the other hand, the details of the construction and operation of the internal component assembly are not of the essence of the present invention.

While the prior electric toothbrush patents identified in the introduction may be referred to for more background with respect to the construction and operation of the electro-mechanical brush driving system, FIGS. 7a and 7b depict the preferred overall arrangement of the different components. Stub 21 on brush shaft 16 protrudes through a guide 60 and emerges from boot 18 on nose 14. Coupled to brush shaft 16 is a driven gear 62 mounted in a coupling 64 by a gear pin 66. Motor 34 mounts on coupling 64 and coupling 64, in turn, is mounted above a battery carrier 68 atop a bobbin 70. A foam separator 72 seats atop battery 32. When assembled, a charging core 72a sets inside bobbin 70. An O-ring 74 completes a seal when plug 46 is screwed into place.

Affixed to carrier 68 is a contour strip 76 on which is mounted a diode 78, a diode 80 and a reed switch 82. A seal 84 seats within an opening 86 formed in the bite of the U-shaped wall of upper shell 38. Projecting through seal 84 is one end 88 of a switch operator 90 in the lower end portion of which end portion is secured a magnet 92. Switch button 28 is secured on the upper end of operator 90 and is exposed outside seal 84 for operation by the user. When assembled, magnet 92, of course, is located in the vicinity of reed switch 82 for controlling operation of the latter.

The arrangement shown is one in which driven gear 62 includes an eccentric pin 94 which seats within an opening 96 in brush shaft 16 so as to effect an oval motion of bristles 26 of the brushhead. If desired, other motion-translating approaches could be used for obtaining a different path of bristle motion.

While the ultimate product may be increased or decreased in actual size from that which is approximately shown in FIG. 2 as submitted with this application, highly successful dimensions in practice were as follows:

Outer shell diameter at plug 46, one inch;
Distance between marks a and b, 1 and 7/8ths inches;
Distance between marks b and c, 2 and 5/8ths inches;
Distance between marks c and d, 3/8ths inch; and
Distance between marks d and e, 1 and 5/8ths inch;
Nose 14 had a diameter of ½ inch, the distance between marks f and g was 3 and 7/8ths inch, that between marks g and h was about one inch and the distance from marks h to mark j at nose 14 was 1 and ¾ inches. The offset between axes 50 and 52 was about 3/5 inch. The entire housing thus was less than seven inches in length. It is to be noted, however, that these dimensions are merely representative. Minor variations therefrom will not detract from the comfort and facility to be experienced by the user.

It will be readily apparent that different approaches also could be used for mounting the different components with respect to each other. The arrangement shown is advantageous for its achievement of compactness with a resultant minimization of both lengths and widths of handle 12. At the same time, the separation of the different basic components is such as to accommodate both the cross sectional shape of housing 12 and in particular the offset of the brush shaft axis from the geometrical axis of the overall unit. Of course, the specific system illustrated and described includes bobbin 70 and charging core 72a for enabling the recharging of battery 32. In the same way as in the references identified in the introduction, the base or lower end of handle 12 when not in use is seated within the well of a separate charging unit which creates an electromagnetic charging field coupled into bobbin 70. That separate charging coil ordinarily is energized from a standard household electrical recepticle.

When the user takes hold of handle 12, housing 30 is found to be seated snuggly, securely and surprisingly comfortably within the grasp of the user's closed fist. Upon insertion of the brushhead within the mouth of the user, the experience is one of improved facility of guiding the brushhead over the surfaces of the teeth and gums while being able to apply the brushhead even to hard to reach places. Yet, the entire unit is capable of being manufactured economically while yet resulting in an overall electric toothbrush which is highly attractive.

While a particular embodiment of the invention has been shown and described, it will be obvious to those skilled in the art that changes and modifications may be made without departing from the invention in its broader aspects and, therefore, the aim in the appended claims is to cover all such changes and modifications as fall within the true spirit and scope of that which is patentable.

We claim:

1. In a battery powered toothbrush having an elongated housing with a nose defined at one end thereof, said housing being shaped to be grasped by the human hand and within which housing are a battery, a motor energized by said battery, a brush shaft driven by said motor with a stub projecting through said nose of said housing and upon which a brush is secured for use, said housing comprising a generally tubular housing shell within which said battery, said motor and said shaft are mounted and which comprises:

an upper half shell of U-shaped exterior cross section over a substantial portion of its length;

a switch button located on said upper half shell at a location toward said nose relative to said substantial portion;

a lower half shell mated to said upper half shell in definition of said housing and being of semi-cylindrical exterior cross section over a similar substantial portion of its length; and said substantial portions of said half shells defining a longitudinal geometric axis, in which said stub projects along a working axis parallel to but spaced in the direction away from said upper shell a predetermined distance from said geometric axis, and in which beyond said substantial portions toward said nose said half shells smoothly curve downwardly in accommodation of said predetermined distance; the downward curve of said upper shell beyond its substantial portion being substantially uniform along its length to said nose, the downward curve of said lower shell is completed in a distance beyond its substantial portion toward said nose to define an arcuate abutment for providing finger support opposite said switch button, and a generally flat surface defined beyond said abutment and laterally spaced from said working axis to the opposite side thereof from said geometric axis.

2. A toothbrush housing as defined in claim 1 in which the distance along said substantial portions approximates the width of the adult human hand.

3. A toothbrush housing as defined in claim 2 wherein at the base end of said housing opposite said nose said shells merge smoothly into a cylinder and the inner wall of said cylinder threadably receives a closing plug.

4. A toothbrush housing as defined in claim 2 in which the widths and heights of said shells smoothly decrease from said substantial portions to said nose.

5. A toothbrush housing as defined in claim 4 in which beyond said substantial portion thereof said lower shell merges into a rearwardly tapering flat.

6. A toothbrush housing as defined in claim 4 in which beyond said substantial portion thereof said upper shell gradually changes to semi-cylindrical at said nose.

* * * * *

UNITED STATES PATENT OFFICE
CERTIFICATE OF CORRECTION

Patent No. 5,341,534          Dated August 30, 1994

Inventor(s) Andrew Serbinski, Steve O. Mork & Roberta L. Callghan

It is certified that error appears in the above-identified patent and that said Letters Patent is hereby corrected as shown below:

Column 1, line 55: after "drawings," -- in -- should be inserted.

Column 3, line 10: "Al" should read -- to form an abutment or finger rest, --.

Column 3, line 45: "component" should read -- components --.

Column 3, line 67: "bite" should read -- bight --.

Column 4, line 23: the semicolon "(;)" should be a period -- (.) --.

Signed and Sealed this

Twenty-second Day of November, 1994

Attest:

BRUCE LEHMAN

*Attesting Officer*     *Commissioner of Patents and Trademarks*